US00PP18477P3

(12) United States Plant Patent
Carruth et al.

(10) Patent No.: US PP18,477 P3
(45) Date of Patent: Feb. 12, 2008

(54) MINI-FLORA ROSE PLANT NAMED 'WEKCLAUNI'

(50) Latin Name: *Rosa hybrida*
Varietal Denomination: WEKclauni

(75) Inventors: Thomas Carruth, Altadena, CA (US); Christian Bedard, Brea, CA (US)

(73) Assignee: Nor'East Miniature Roses, Arroyo Grnade, CA (US)

( * ) Notice: Subject to any disclaimer, the term of this patent is extended or adjusted under 35 U.S.C. 154(b) by 245 days.

(21) Appl. No.: 11/284,023

(22) Filed: Nov. 21, 2005

(65) Prior Publication Data

US 2007/0118940 P1 May 24, 2007

(51) Int. Cl.
*A01H 5/00* (2006.01)

(52) U.S. Cl. ..... Plt./122

(58) Field of Classification Search ..... Plt./122
See application file for complete search history.

*Primary Examiner*—Kent Bell
*Assistant Examiner*—Annette H Para

(57) ABSTRACT

'WEKclauni' is a new variety of Mini-flora rose suitable for garden decoration, having flowers of dark red coloration, on an upright and fully branched plant.

1 Drawing Sheet

CROSS REFERENCE

Comparison with the Closest Commercially Available Cultivar: The closest commercially available cultivar to the new variety is the seed parent 'POUlclaus', as described below.

Genus and species: The present invention relates to a new *Rosa hybrida* plant.

Varietal denomination: The new plant has the varietal denomination 'WEKclauni'.

BACKGROUND OF THE INVENTION

This invention relates to a new and distinct variety of mini-flora rose. It was created in a greenhouse in Upland, Calif., by crossing the variety known as 'POUlclaus' (U.S. Plant Pat. No. 9,063) as its seed parent and the variety known as 'JAColber' (U.S. Plant Pat. No. 11,265) as its pollen parent.

COMPARISON WITH PARENTS

The new rose may be distinguished from its seed parent, 'POUlclaus' by the following combination of characteristics: whereas 'WEKclauni' bears medium sized flowers (about 5.4 to about 8.0 cm. in diameter) of double petalage (about 15 to 28 petals), 'POUlclaus' bears significantly smaller flowers (about 5 to about 6.5 cm. in diameter) of semi-double petalage (about 14 to 18 petals). The mature growing habit of the new variety is upright and somewhat open and of moderately low height (about 46 to about 52 cm. in height), whereas the mature growing habit of the seed parent is bushy, compact and upright with significantly taller height (about 65 to about 75 cm. in height).

The new variety may be distinguished from its pollen parent, 'JAColber' by the following combination of characteristics: whereas 'WEKclauni' bears medium sized flowers (about 5.4 to about 8.0 cm. in diameter) of double petalage (about 15 to 28 petals), 'JACcolber' bears significantly larger flowers (about 13.0 to about 14.0 cm. in diameter) with significantly heavier petalage (about 30 to 35 petals). The new variety is classified as a mini-flora rose with a moderately low mature growing habit of about 46 to about 52 cm. in height, whereas the pollen parent is classified as a Hybrid Tea with an upright significantly taller mature growing habit of about 180 cm. in height.

BRIEF SUMMARY OF THE INVENTION

Among the features which distinguish the new variety from other presently available and commercial rose cultivars known to the inventor are the following combination of characteristics: its even dark-red coloration that lasts throughout the life of the flower, its combined red and golden-yellow coloration on both the anthers and filaments, its red suffusion on the stipule, its stipitate glands on the major stems, branches and new shoots and its red suffusion on the inner surface of the sepal that appears as the flower ages. The plant has an upright, fully branched and somewhat open growth habit, suitable for outdoor garden decoration.

Asexual reproduction of the new variety by budding as performed in Kern County and Upland, Calif., shows that the foregoing and other distinguishing characteristics come true to form and are established and transmitted through succeeding asexual propagations. 'WEKclauni' may be asexually propagated by cuttings, budding and grafting. The budding and grafting successfully occurred on the plant/rootstock *Rosa hybrida* cv. 'Dr. Huey'.

BRIEF DESCRIPTION OF THE DRAWING

The accompanying photograph illustrates the new variety and shows the flowering thereof from bud to full bloom depicted in color as nearly correct as it is possible to make in a color illustration of the character. Throughout this specification, color references and/or values are based upon the Colour Chart of The Royal Horticultural Society (1966)

except where common terms of color definition are employed.

DETAILED BOTANICAL DESCRIPTION

The following description is of 3 to 4 year-old rose plants of this new variety grown outdoors in Upland, Calif. in the month of September. Phenotypic expression may vary with environmental, cultural and climatic conditions, as well as differences in conditions of light and soil.

FLOWER

The new variety usually bears its flowers singly. Flowers are borne on strong short stems (about 12 to about 22 cm.). Outdoors, the plant blooms abundantly and nearly continuously during the growing season. The flowers have a very slight tea fragrance.

BUD

The peduncle is about 2.2 to about 3.9 cm. in length, of moderately heavy caliper (about 0.2 to about 0.3 cm. in diameter), and usually erect and somewhat stiff. It is moderately smooth, with many stipitate glands and numerous hairs. Peduncle color is a medium green, between 144A and 139C, often heavily suffused, especially on the side exposed to the sun, with between 183A and 187B, from the greyed-purple group.

Before the calyx breaks, the bud is about 0.7 to about 1.7 cm. in diameter at the widest point, about 1.0 to about 1.9 cm. in length, and moderately ovoid to somewhat pointed in shape. The surface of the bud bears few foliaceous appendages and some stipitate glands, usually with slender entire foliaceous parts extending beyond the tip of the bud about ¼ or more of its length. Bud color is between 144A and 139C often heavily suffused, especially on the side exposed to the sun, with between 187A and 183A.

The sepals are about 1.8 to about 3.0 cm. in length and about 0.6 to about 0.9 cm. in width at the widest point. The outer surface color of the sepal is between 144A and 139C often heavily suffused, especially on the side exposed to the sun, with between 187A and 183A. The inner surface color of the sepal is lighter, between 138A and 139D. After the sepals open, the inner surface color is often heavily suffused, especially on the area exposed to the sun, with between 187A and 183B. The sepals are covered with fine wooly tomentum; sepal margins are lined with many stipitate glands and hairs.

The receptacle of the flower is of medium length (about 0.6 to about 0.8 cm.) and somewhat heavy in caliper (about 0.6 to about 0.8 cm. in diameter). The receptacle is globular in form. Its surface is smooth with some hairs and thick fleshy walls. The receptacle color is between 144A and 139C sometimes lightly suffused, especially on the side exposed to the sun, with between 183A and 187B.

As the petals open (after the calyx breaks), the bud is about 1.3 to about 2.5 cm. in diameter at the widest point, about 1.7 to about 2.5 cm. in length, and moderately ovoid to somewhat pointed in form. The color of the under and upper surfaces of the newly opened petals is a very dark red, between 187A and darker than 46A. At the point where the petal attaches, there is a small zone of a medium green-yellow, between 1D and 3D.

BLOOM

When fully open, the bloom ranges from about 5.4 to about 8.0 cm. in diameter. Petalage is double with about 15 to 28 petals and about 3 to 7 petaloids irregularly arranged. When partially open, the bloom form is globular to somewhat cupped, and the petals are loosely spiraled to cupped with petal edges slightly reflexed outward. When fully open, the bloom form is cupped, and the petals are more loosely cupped with petal edges moderately reflexed outward.

PETALS

The substance of the petals is somewhat slight and of moderately thin thickness, with upper surfaces moderately velvety and under surfaces matte to slightly shiny. The petals are about 1.8 to about 3.1 cm. in length and about 1.3 to about 3.2 cm. in width at the widest point. Petal margins are entire.

The outer petals are nearly round in shape with rounded apices.

The inner petals are nearly rounded to somewhat obovate in shape with rounded apices and sometimes emarginated, with a slight notch.

Petaloids are about 1.4 to about 1.9 cm. in length and about 0.5 to about 1.4 cm. in width at the widest point. Petaloids are shaped moderately obovate to somewhat oblanceolate in shape with rounded apices and sometimes emarginated, with one slight notch.

NEWLY OPENED FLOWER

The under surface color of the outer, intermediate and inner petals is between 53A, Cardinal Red, and darker than 46A, Current Red. The upper surface color of the outer, intermediate and inner petals is between darker than 53A and 46A, and sometimes moderately blushed toward the petal edges with near 187A, from the greyed-purple group. At the point where the petal attaches on the upper and under surfaces, there is a small zone of near 5C, Dresden Yellow.

The under and upper surface color of the petaloids are similar in coloration to the upper and under surfaces of the intermediate and inner petals.

The general tonality of the newly opened flower is between darker than 53A and 46A, and sometimes moderately blushed toward the petal edges with near 187A.

THREE-DAY-OLD FLOWER

The under surface color of the outer, intermediate and inner petals is between 53A and darker than 46A. The upper surface color of the outer, intermediate and inner petals is between 53A and 46A sometimes moderately blushed toward the petal edges with near 187A. At the point where the petal attaches on the upper and under surfaces, there is a small zone of near 4D, Primrose Yellow.

The under and upper surface color of the petaloids are similar in coloration to the upper and under surfaces of the intermediate and inner petals.

The general tonality of the three-day-old flower is between 53A and 46A sometimes moderately blushed toward the petal edges with near 187A.

On the spent bloom, the petals usually drop off cleanly.

In September in Upland, Calif., blooms on the bush growing outdoors generally last about four to five days. Cut roses from plants grown outdoors and kept at normal indoor living temperatures generally last about four to five days.

MALE REPRODUCTIVE ORGANS

Stamens are many in number (average about 140) and are arranged regularly about the pistils; a few are mixed with petaloids. The filaments are of medium length (about 0.3 to about 0.7 cm.) most with anthers. Filaments are between 21B, Maize Yellow, and 15A, Buttercup Yellow, at the base suffusing to a deep orange-red, between 34B and 33A in color near the top. The anthers are somewhat small for the class and all open approximately at the same time. When immature, anther color is near 53B, Cardinal Red, at the center and surrounded by near 25B, Nasturtium Orange, and appearing black, near 202A, in the center surrounded with near 163C, from the Greyed-Orange group, at maturity.

Pollen is moderately abundant and a light orange-yellow, between 14D and 12D in color.

FEMALE REPRODUCTIVE ORGANS

Pistils vary in number (average about 60). The styles are moderately even, average in length (about 0.4 to about 0.7 cm.), somewhat thin in caliper, and loosely bunched to somewhat separated. Stigma color is near 18D, a very pale yellow. Style color is a very light green-yellow, between 1D and 2D, usually heavily suffused near the top with near 53A, Cardinal Red. Ovaries are usually all enclosed in the calyx.

Hips are of moderately long length (about 1.3 to about 1.9 cm.), globular in form, and a bright orange, between 24A and 25B, in color when ripe. The hip surface is smooth with thick fleshy walls. The sepals are moderately permanent and usually straight in shape.

The seeds are irregularly rounded, smooth in texture, approximately 19 to about 26 per hip, about 0.4 to about 0.7 cm. in diameter at the widest point and between 161B and 162C, from the greyed-yellow group, in color.

FOLIAGE

The compound leaves are usually comprised of three to seven leaflets and are borne in moderately sparse quantities. The five-leaflet leaves are about 4.4 to about 10.1 cm. in length and about 3.4 to about 6.7 cm. in width at the widest point, somewhat thin to moderately leathery in texture, and semi-glossy to almost matte in finish. The terminal leaflets are about 2.3 to about 4.0 cm. in length and about 1.4 to about 2.3 cm. in width at the widest point, shaped ovate to somewhat oval with acute apices and rounded bases. Their margins are usually simply serrate.

The upper surface color of the mature leaf is a very dark green, between 147A and 137B. The under surface color of the mature leaf is a little lighter, between 147B and 138C. The upper surface color of the young leaf is between 147A and 138B, usually heavily suffused on the very edge on the leaf with between 187A and 183A, from the greyed-purple group. The under surface color of the young leaf is between 138B and 138C, usually moderately suffused with between 187B and 183B.

The rachis is somewhat light in caliper and moderately rough. The upper side is moderately grooved with some hairs and stipitate glands on the edges of the grooves. The under side of the rachis is moderately rough with some stipitate glands and few small prickles. The rachis color is between 144B and 146C often heavily suffused especially on the upper side of the young leaves with between 187A and 183A.

The stipules are about 0.7 to about 1.1 cm. in length and of medium width (about 0.3 to about 0.4 cm.) with moderately short straight points that usually turn out at an angle of more than 45 degrees and often recurve toward the stem. The stipules color is a medium yellow-green, between 144A and 146B, and sometimes lightly suffused especially on the young leaves with between 187C and 183B.

The petiole is somewhat light in caliper and moderately rough. The upper side is moderately grooved with some hairs and stipitate glands on the edges of the grooves. The under side of the rachis is moderately rough with some stipitate glands and few small prickles. The petiole is about 0.6 to about 1.1 cm. in length and about 0.1 to about 0.15 cm in diameter at the widest point. The petiole color is between 144B and 146C often heavily suffused especially on the upper side of the young leaves with between 187A and 183A.

The plant displays an average degree of resistance to powdery mildew and rust as compared to other commercial varieties grown under comparable conditions in Upland, Calif. This new cultivar has been tested winter hardy in United States Department of Agriculture zones 5 through 10, with winter protection recommended for zones 6 and colder, and with comparable heat tolerance in Horticultural Society heat zones 10 through 1.

PLANT

The plant has an upright and somewhat open and moderately low height growing habit (about 46 to about 52 cm. in height and about 33 to about 41 cm. spread at the widest point), with full branching. It displays moderately vigorous growth and the canes are of somewhat heavy caliper for the class, with main canes having a diameter of 0.9 to 2.5 cm and primary laterals generally having a diameter between 0.48 cm and 0.62 cm. The diameter of flowering stems averages 0.25 cm.

The color of the major stems is a dark yellowed-green, between 146A and 137C. They bear some large prickles that are about 0.4 to about 0.7 cm. in length. The large prickles are angled slightly downward with a moderately short length oval base; prickle color is between 166D and 165B, from the greyed-orange group. The major stem bears many small prickles of similar shape and coloration and some stipitate glands.

The color of the branches is slightly lighter, between 146B and 137C. They sometimes bear large prickles, which are of similar size and shape to the large prickles on the major stems; prickle color is between 160C and 162C, from the greyed-yellow group. The branches bear many small prickles of similar shape and coloration and some stipitate glands.

The color of the new shoots is a lighter, between 144A and 137D, and sometimes moderately suffused with between 187B and 183A. They sometimes bear some large prickles, which are of similar size and shape to the large prickles on the major stems; prickle color is between 160C and 162C sometimes moderately suffused with between 187B and 183A. The shoots bear many small prickles of similar shape and coloration and some stipitate glands.

We claim:

1. A new and distinct Mini-flora rose plant of the variety substantially as described and illustrated herein, with flowers of a dark red tonality on a vigorous and upright plant.

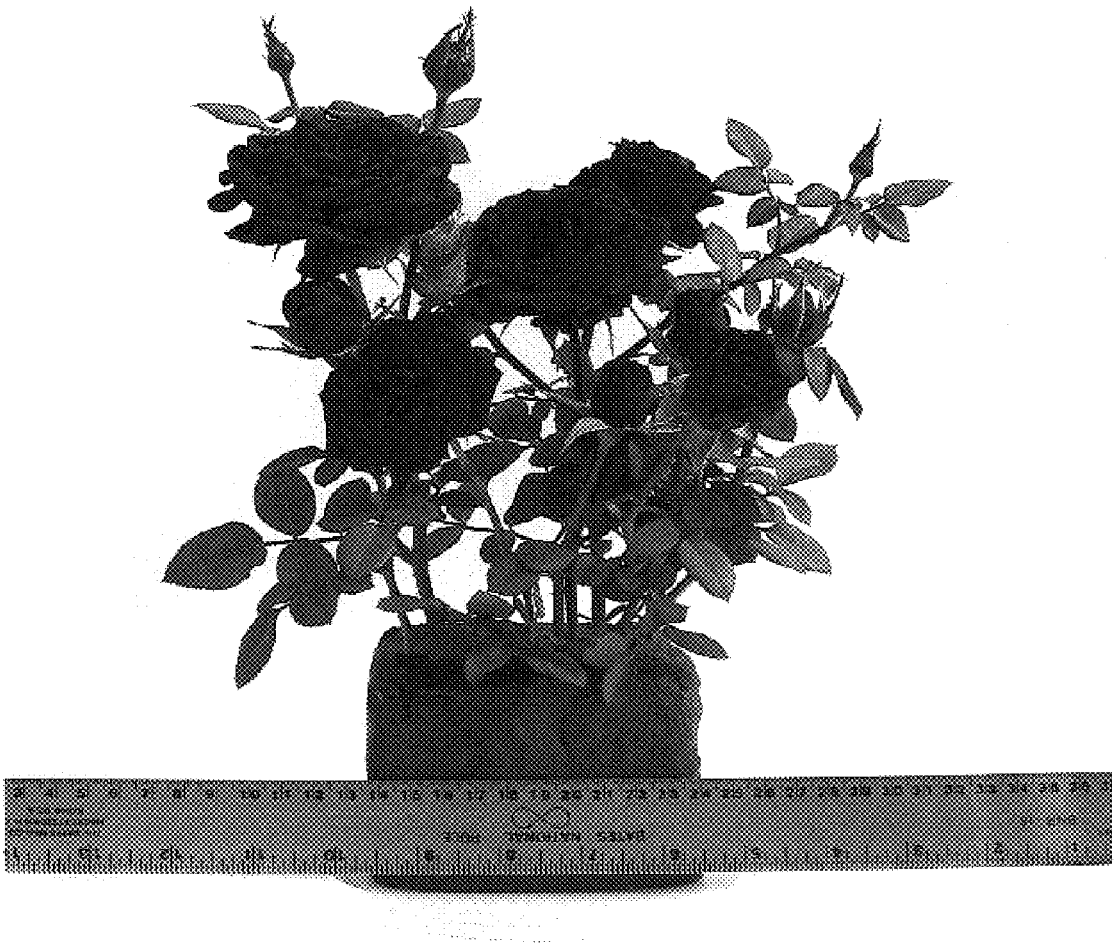

* * * * *